United States Patent [19]
Dolphin et al.

[11] Patent Number: 5,077,394
[45] Date of Patent: Dec. 31, 1991

[54] PORPHYRINS AND USES THEREOF

[75] Inventors: David H. Dolphin, Vancouver, Canada; Taku Nakano, Mie, Japan; Thomas K. Kirk, Verona, Wis.; Tilak P. Wijesekera, Vancouver, Canada; Roberta L. Farrell, Danvers; Theodore E. Maione, Concord, both of Mass.

[73] Assignee: Sandoz Ltd., Basel, Switzerland

[21] Appl. No.: 455,663

[22] Filed: Dec. 21, 1989

Related U.S. Application Data

[60] Division of Ser. No. 181,859, Apr. 15, 1988, Pat. No. 4,892,941, which is a continuation-in-part of Ser. No. 39,566, Apr. 17, 1987, abandoned.

[51] Int. Cl.$^5$ .................... C07G 1/00; C07C 29/48; C07D 301/03
[52] U.S. Cl. ............................ 530/505; 549/523; 549/524; 568/825; 568/836; 568/910
[58] Field of Search ............... 530/505; 549/523, 524; 568/825, 836, 910; 514/22

[56] References Cited

PUBLICATIONS

Wright et al., J. Wood Chem. & Tech., 4(1), 1984, pp. 61–74.
Shimada et al., Biochem. Biophysis Res. Comm., 122(3), 1984, pp. 1247–1257.
Dolphin, The Biochemistry of Iron, D. Reidel Publishing Co., (1982), pp. 283–294.

Primary Examiner—Richard L. Raymond
Attorney, Agent, or Firm—Gerald D. Sharkin; Richard E. Vila; Joanne M. Giesser

[57] ABSTRACT

Disclosed are tetraphenyl porphyrins which are beta-substituted by fluoro or chloro and/or bear electronegative substituents on the phenyl including one or two water solubilizing substituents. The new porphorins are particularly suitable as catalysts in a variety of oxidative reactions and methods.

25 Claims, No Drawings

PORPHYRINS AND USES THEREOF

This is a division of application Ser. No. 07/181,859, filed Apr. 15, 1988, now U.S. Pat. No. 4,892,941, which in turn is a continuation-in-part of application Ser. No. 07/039,566, filed Apr. 17, 1987, now abandoned.

Certain metal-containing porphyrin compounds are known to be useful as chemical reagents of a catalytic nature, more particularly in directing certain oxidative processes. A biomimetic is a compound which mimics the activity of a biologic compound. Certain porphyrins have been studied in relation to their ability to mimic the class of enzymes known as ligninases which participate in the natural process of wood degradation and modification by acting on lignin. The activity of these porphyrins on lignin-model substrates has been also indicated by researchers.

Known porphyrins have been judged to suffer certain drawbacks by being deficient in the combination of properties desired for many candidate uses, such as in the pulp and paper industry. Included among the observed problems with porphyrins is one of instability, often due to the potential for one porphyrin to adversely affect another. Efficiency in oxidative reactions is another consideration. Also, for many important potential uses, water solubility combined with other desired properties is particularly being sought.

BRIEF SUMMARY OF THE INVENTION

The present invention provides new and improved metal-containing porphyrin compounds, improved processes for their production and their use. Included among the new porphyrins are those which combine stability, high oxidative potential and water solubility.

Also provided in part by this invention are porphyrins which contain a high number of chloro- and fluoro-groups which increase the oxidative potential to an unexpectedly high level. Porphyrin compounds of this invention are active in a variety of reactions.

One important group of reactions involves or relates to the oxidation of lignin and lignin-model compounds. Other reactions that they catalyze include the conversion of alkanes to alcohols and the conversion of alkenes to epoxides. Further, they are able to oxidize organic environmental pollutants such as chlorinated biphenyls and dioxin into harmless compounds.

DETAILED DESCRIPTION OF THE INVENTION

The porphyrins of the present invention have the following formula I:

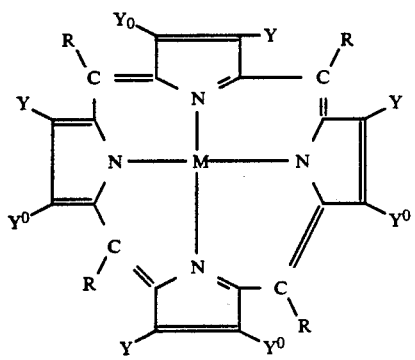

wherein M is a transition metal capable of sustaining oxidation, and if desired may also be joined to one or more axial ligands in addition to the four nitrogen groups, each Y and $Y^o$ is independently H, fluoro or chloro, each R ring is

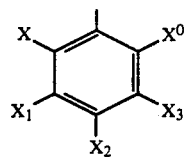

X and $X^o$ are independently H or an electronegative group which is not a water solubilizing group, e.g. X and $X^o$ are independently, fluoro, chloro, bromo, or $NO_2$, $X_1$, $X_2$ and $X_3$ are independently H or an electronegative group, including water solubilizing electronegative groups, including without limitation fluoro, chloro, bromo, $SO_3H$, COOH or $NO_2$, subject to the provisos that 1) When none of $X_1$, $X_2$ and $X_3$ is not a water solubilizing group, then at least one Y and $Y^o$ on each porphyrin ring is other than H, 2) when Y and $Y^o$ are both H, at least one but not more than two of $X_1$, $X_2$ and $X_3$ is a water solubilizing group, e.g. $SO_3H$ or COOH, and at least two of X and $X^o$ and the $X_1$, $X_2$ and $X_3$ which are not a water solubilizing group are independently an electronegative group which is not a water solubilizing group, e.g. fluoro, chloro, bromo or $NO_2$, and 3) no more than two of $X_1$, $X_2$ and $X_3$ are water solubilizing groups, or the water soluble salts thereof in which said water solubilizing groups are in corresponding water soluble salt form.

Particular subgroups of the compounds of the formula I are the compounds of the formulae Ia and Ib.

The compounds of the formula Ia are those with reference to the structural formula I in which:

a) at least one of Y and $Y^o$ on each porphyrin ring is fluoro or chloro and the other is H, fluoro or chloro, b) X and $X^o$ are independently H, fluoro, chloro, bromo or $NO_2$, c) $X_1$, $X_2$ and $X_3$ are independently H, fluoro, chloro, bromo, $SO_3H$, COOH or $NO_2$, provided that no more than two of $X_1$, $X_2$ and $X_3$ are $SO_3H$ or COOH, and d) M is as above defined.

The compounds of the formula Ib are those with reference to the structural formula I in which a) Y and $Y^o$ are independently H, fluoro or chloro, b) X and $X^o$ are independently H, fluoro, chloro, bromo or $NO_2$, c) $X_1$, $X_2$ and $X_3$ are independently H, fluoro, chloro, bromo, $SO_3H$, COOH and $NO_2$ with the provisos that i) at least one but not more than two of $X_1$, $X_2$ and $X_3$ are $SO_3H$ or COOH, and ii) at least two of X, $X^o$, $X_1$, $X_2$ and $X_3$ is fluoro, chloro, bromo or $NO_2$, and d) M is as above defined.

The preferred compounds of the formula Ia have one or more of the following features: a) both Y and $Y^o$ on each porphyrin ring is fluoro or chloro; b) at least two of X, $X^o$, $X_1$, $X_2$ and $X_3$ are fluoro or chloro, more particularly with X and $X^o$ being fluoro or chloro, and c) M is Fe, Cr, Mn or Ru. More preferred compounds of the formula Ia have one or more of the following features: a) both Y and $Y^o$ on each porphyrin ring is chloro, b) at least two of X, $X^o$, $X_1$, $X_2$ and $X_3$ are chloro, more particularly with X and $X^o$ being chloro, and c) M is Fe.

The preferred compounds of the formula Ib have one or more of the following features: a) Y and $Y^o$ on each porphyrin ring is independently H or chloro, b) one of $X_1$, $X_2$ and $X_3$ is $SO_3H$, c) at least two of X, $X^o$, $X_1$, $X_2$ and $X_3$ are fluoro or chloro, more particularly with X and $X^o$ being fluoro or chloro, and d) M is Fe, Cr, Mn or Ru. More preferred compounds of the formula Ib have one or more of the following features: 1) Y and $Y^o$ on each porphyrin ring are independently H or chloro, b) one of $X_1$, $X_2$ and $X_3$ is $SO_3H$, c) at least two of X, $X^o$, $X_1$, $X_2$ and $X_3$ are chloro, more particularly with X and $X^o$ being chloro, and d) M is Fe. Another preferred subclass of the compounds of the formula Ib are those in which one of Y and $Y^o$ on each porphyrin is other than H, more particularly those in which both Y and $Y^o$ are fluoro or chloro.

With regard to each R ring as described above, each R ring will contain the minimum substitution provided for above, but the positioning and number of substitutions above the minimum on each R ring may vary. Preferably, each R ring is the same.

In general, it is preferred that only one of $X_1$, $X_2$ and $X_3$ is a water solubilizing group. It is also more particularly preferred that when one of Y or $Y^o$ is to be other than H, that both be other than H.

A subclass of the compounds of the formula Ib described in application Ser. No. 039,566 of Apr. 17, 1987, in which Y and $Y^o$ are H, X and $X^o$ are each chloro, $X_1$ and $X_2$ are H and $R_3$ is an electronegative group including a water solubilizing group, including those in which any water solubilizing group is in free acid form and those with and without ligands such as the chloride ligand form.

The compounds of the invention having $SO_3H$ or COOH groups are water soluble and the invention also includes such water soluble compounds in which such groups are in water soluble salt form with a cation of a base such as an alkali metal (sodium, potassium or lithium), an alkaline earth metal, or an ammonium cation, preferably an alkali metal or ammonium cation. Such salt forms may be prepared by reacting a compound of the formula I with a base by conventional procedures.

M may be any transition metal which is capable of sustaining oxidation Examples of preferred metals include Fe, Cr, Mn, Ru and Co. Particularly preferred metals are Fe, Ru, and Mn. Additionally the metal may be joined to a ligand. The axial ligands, usually one or two but occasionally more, may be virtually any group which is capable of forming a single hydrolyzable bond with the M, as known in the art. Examples of axial ligands by way of illustration only include —$OCH_3$, —OH, amines, halide ions, particularly chloride, and water.

In order to construct some of the catalysts of the present invention it may be desirable to use an intermediate porphyrin compound which contains in place of its M group a metal ($M^o$) such as Ni or Zn. While these particular compounds may not be particularly capable of sustaining oxidation, the Ni or Zn (and Fe) activates the porphyrin ring, allowing it to be substituted with the desired fluoro or chloro group. When effecting β-substitution and both of X and $X^o$ are H, it is particularly desirable to employ the compounds in which M is Ni. The compounds of the formula I in which M is replaced by Zn or Ni are useful intermediates, particularly the Ni intermediates. By "capable of sustaining oxidation" is meant a metal capable of being oxidized in the presence of an oxidizing agent and then being reduced during participation in the desired oxidation reaction, such that it can again be oxidized by the oxidizing agent. In this sense the porphyrins are referred to as catalysts since typically minor amounts can be used and essentially replenished in the reaction systems.

When M is joined to, e.g. a halo ligand (F, Cl, Br or I), the compound of the formula I can be considered a salt form, e.g. in the relationship $M^+$ and $HAL^-$ wherein HAL is the halogen. Such salts result when M is in the plus three valence state, e.g. $Fe^{+++}$, or in higher valence states, as is known.

As used throughout the specification and claims, the following definitions will apply:

Free base porphyrin—a porphyrin ring which does not contain a metal group;

Electronegative group—a chemical group which is electronegative and which can withdraw electrons either inductively or via conjugation, also referred to as "electron-withdrawing" groups. Examples of such groups include, but are not limited to halogens (e.g. Cl—, Br—, F—), $HO_3S$— and $O_2N$—;

Particular embodiments of this invention include the following species:

| Example | Metal | Y and $Y^o$ Groups | R Groups |
|---|---|---|---|
| Example 5 | Fe | Cl | 2,6 dichlorophenyl |
| Example 6 | Fe | Cl | Pentachlorophenyl |
| Example 4 | Fe | Cl | Phenyl |
| Example 8 | Fe | Cl | 2,6-dichloro, 3-sulphanoto-phenyl |
| Example 7 | Fe | Cl | 4-sulphanotophenyl |
| Example 2 | Fe | H | 2,6-dichloro,3-sulphanoto-phenyl |

Also within the scope of this invention are the non-metal containing intermediate having the following formula:

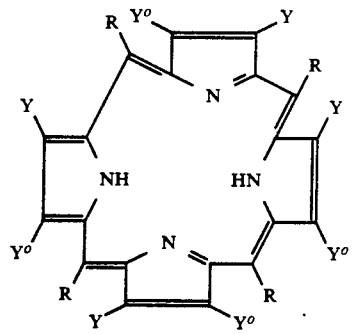

wherein each Y and $Y^o$ is independently H, flouro or chloro, and each R ring is

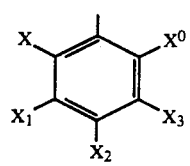

X and $X^o$ are independently H or a non-water solubilizing electronegative group, e.g. fluoro, chloro, bromo, or $NO_2$, $X_1$, $X_2$ and $X_3$ are independently H or an electronegative group, including water solubilizing electronegative groups, including without limitation fluoro, chloro, bromo, $SO_3H$, COOH or $NO_2$, subject to the provisos that 1) When any of $X_1$, $X_2$ and $X_3$ are not a water solubilizing group, then at least one Y and $Y^o$ on each porphyrin ring is other than H, 2) when Y and $Y^o$ are both H, at least one but not more than two of $X_1$, $X_2$ and $X_3$ is a water solubilizing group, e.g. $SO_3H$ or COOH, and at least two of X and $X^o$ and the $X_1$, $X_2$ and $X_3$ which are not a water solubilizing group are independently an electronegative group which is not a water solubilizing group, e.g. fluoro, chloro, bromo or $NO_2$, and 3) no more than two of $X_1$, $X_2$ and $X_3$ are water solubilizing groups, or the water soluble salts thereof in which said water solubilizing groups are in corresponding water soluble salt form.

Also included in the scope of the present invention is a process for producing the above compounds. It has been found that the substituted porphyrin rings (hereinafter referred to as β-substitution) can be made by two routes. The first route is to start with unsubstituted porphyrin which does not contain any metal (hereinafter referred to as free base porphyrin), and metallize it. This can be accomplished by dissolving the free base porphyrin in a solvent such as DMF or $CH_3COOH$. Next the metal is added. This may be in the form of metal salts of any desired valence, for example M(II), or M(III) or a covalent form such as M(O) where M is the metal. While virtually any metal may be used, preferred metals include Ni, Fe, and Zn, and particularly preferred metal salts include $Fe(CO)_5$, $FeCl_2$ and $FeCl_3$.

After the free base porphyrin is metallized, the next step is β-substitution of the porphyrin ring. This step may be done by contacting the porphyrin ring with an electrophilic reagent. Examples include electrophilic chlorinating or fluoronating agents such as molecular chlorine, molecular flourine, and chloro-succinamide (for halogenations) or high valence metal halides $CoX_3$, $CeX_4$, or $MnX_3$ (X being a halogen such as chloro) or electrophilic agents which donate $-NO_2$ or $-SO_3H$ groups (for non-halogenation substitutions).

Next, phenyl groups may be substituted, if desired, according to standard procedures.

When a metal such as Ni or Zn is used, it is replaced by a metal capable of sustaining oxidation.

Alternatively, the steps of metallization, β-substitution, and substitution of the phenyl rings may be carried out in whichever order is considered the most convenient. This invention thus comtemplates additional reaction schemes which include the following:

| | | | | |
|---|---|---|---|---|
| 1. | free base → porphyrin | metallation → | β-substitution → | ø-ring substitution |
| 2. | free base → porphyrin | substitution of → ø-rings | metallation → | β-substitution |
| 3. | free base → porphyrin | metallation → | substitution of → ø-rings | β-substitution |
| 4. | free base → porphyrin | metallation → | β-substitution → | substitution of ø-rings |

It has been found that the compounds of formula I are very stable and powerful catalysts in the presence of a variety of oxidants. In addition, the compounds of the formula Ib are water-soluble. Also, since the water solubilizing groups, e.g. sulfonate groups, are election withdrawing, the stability of the catalyst is increased as it now is more difficult to destroy by oxidation. Additionally this electron deficiency is transmitted to the metal atom making for an even more powerful, as well as robust catalyst. The porphyrin catalysts are functional at virtually any pH, and at high temperatures (150° C. or more); thus they may be used in many commercializable processes.

The compounds of the formula I may be used as oxidation catalysts in the variety of processes in which prior art optionally substituted phenyl porphyrins have been indicated as useful, the compounds of the formula I which are water soluble being particularly useful in those processes in which water solubility is desired or required. Such processes include, merely by way of illustration only, the oxidation of alkanes (including cycloalkanes), the oxidation of alkenes (including cycloalkenes), the oxidative conversion of lignin model compounds which are converted by the lignin modifying and degrading fungal enzymes also known as ligninases, the use in the modification or degradation of lignin, the use in the treating of wood in various forms such as wood chips or pulp to assist in or effect pulping or bleaching. Particular pulping-related processes of interest for the use of the water soluble compounds Ib for assisting in or effecting a modification or degradation of lignin are the well-known mechanical pulps such as thermal mechanical pulps and in the treatment of kraft pulps such as to effect bleaching. The compounds of the formula I which are water insoluble may also be used in solvent pulping such as the known organosolv pulping process. Other uses include the decomposition of organic contaminants in waste streams such as the chlorinated organic compounds in E1 effluent from the kraft pulp chlorine bleaching process. Of particular interest is the use of the formula I as catalysts in the catalytic oxidation of alkanes (including cycloalkanes) for the hydroxylation of the same (or ultimate keto formation) and in the catalytic oxidation of alkenes (including cycloalkenes) to form epoxides (epoxidation). Such hydroxylations and epoxidation are known reactions which are commonly carried out in an inert organic solvent, but water containing systems may also be used; hence both the water soluble and water insoluble compounds of the formula I may be used in such processes. In general, in addition to indicated advantages of the porphyrins of the invention, the porphyrins may be used over a wide range of reaction temperatures including high temperatures up to 150° C. or even higher, and over a wide range of pH's which may extend from about 1 to 14, more suitably from pH 2 to pH 12.

The following examples illustrate but do not limit the invention.

EXAMPLE 1

Synthesis of Porphyrins

Step 1, Preparation of tetra(2,6 dichlorophenyl)porphinatoiron (III) chloride ($TPPFCl_8$)

A compound in which:
M = Fe, axially ligated to Cl;
X = Cl;
$X^o$ = Cl;
$X_1$, $X_2$, $X_3$ = H;

Y, Y$^o$=H.

Pyrrole (redistilled: 6.94 mL, 100 mM), 2,6-dichlorobenzaldehyde (17.5 g; 100 mM), anhydrous zinc acetate (6.6 g; 36 mM) and 2,6-lutidine (150 ml. Note 1) are placed in a 500 ml r.b. flask fitted with a Soxhlet extractor surmounted by a reflux condenser. Anhydrous Na$_2$SO$_4$ is placed in a thimble in the extractor and the reaction mixture is heated at reflux for 5 h (Note 2). After evaporating the lutidine in vacuo, the resulting tarry residue is triturated with toluene (500 ml) and allowed to stand in the refrigerator overnight. The fine purple crystals of the ZnTPPCl$_8$ are filtered and washed thoroughly with cold toluene (Note 3).

The zinc complex is dissolved in CH$_2$Cl$_2$ (250 ml) and is treated with trifluoroacetic acid (25 ml). This mixture is allowed to stir for 6 h (Note 4) and poured into water (300 ml). The organic layer is separated, washed with saturated aq. NaHCO$_3$ (150 ml), and water (2×150 ml) then concentrated after adding methanol. The free base, H$_2$TPPCl$_8$ (Note 5) is collected by filtration, washed with methanol and dried. Yield, 1.26 g.

Step 2, Removal of the Chlorin Impurity

The crude free base from Step 1 is dissolved in CHCl$_3$ (500 mL) and heated to reflux. A solution of 2,3-dichloro-5,6-dicyano-1,4-benzoquinone (DDQ; 600 mg) in dry benzene (40 mL) is added and the heating continues until the absorption at $\lambda$=658 disappeared (Note 6).

The reaction mixture is evaporated to dryness, redissolved in hot CHCl$_3$ (ca. 200 mL) and passed through neutral alumina (100 g; act. I). The oxidant (DDQ) and other impurities adsorb strongly at the origin while the porphyrin elutes cleanly with CHCl$_3$. The porphyrin is crystallized from the CHCl$_3$ solution by concentration and addition of n-hexane.

Step 3, Insertion of Iron

The free base (700 mg) is dissolved in degassed N,N-dimethylformamide (DMF, 400 mL) in a IL 3-necked r.b. flask fitted with a gas inlet tube and a reflux condenser, the third neck being stoppered. The solution is heated to reflux (with N$_2$ or Ar bubbling) and treated with a solution of FeCl$_2$.4H$_2$O (3 g) in degassed DMF (100 mL). Heating is continued and the insertion of iron is monitored using uv-visible spectroscopy. In the Soret region, the single sharp absorption at $\lambda_{max}$=418 changed to a split Soret at $\lambda_{max}$=360/418 while in the visible region, the spectrum changed from $\lambda_{max}$=512, 588 to $\lambda_{max}$=508, 580, 644 (Note 7). Heating is discontinued and air is bubbled through the solution overnight in order to ensure the Fe$^{2+}$ inserted is oxidized to its more stable Fe$^{3+}$ state.

The supernatant DMF solution is decanted from the solid FeCl$_3$, concentrated in vacuo to approximately 200 mL and is treated with dilute HCl (600 mL; 1:1). The hemin precipitates out as a brown solid from a clear yellow solution. The solid is collected by filtration, washed thoroughly with water and dried in a vacuum dessicator.

The crude solid is redissolved in minimum CH$_2$Cl$_2$ and passed through silica gel (act. I) contained in a fritted glass funnel (150M) using CH$_2$Cl$_2$ as the eluting solvent. The unreacted porphyrin elutes cleanly and is recovered by crystallization (ca. 75 mg). The hemin is then eluted using 5% CH$_3$OH in CH$_2$Cl$_2$. This is evaporated to dryness, redissolved in CH$_2$Cl$_2$ and extracted once with Concentrated HCl (equal volume; Note 8).

The organic layer is washed with water (until the water extract is neutral), dried (Na$_2$SO$_4$) and the hemin recovered as shiny purple crystals using n-hexane. A first yield of 550 mg and a second of 60 mg are obtained.

Note 1 Lutidine is refluxed with CaH$_2$ for 2 h and fractionally distilled under N$_2$ at atmospheric pressure. The fraction distilling over at 143.5°-144.5° C. is collected and stored under N$_2$.

Note 2 Water is produced in the reaction, distilled over with the solvent but is retained by the drying agent (Na$_2$SO$_4$) in the Soxhlet while the solvent is recycled.

Note 3 Uv-vis spectrum (in CH$_2$Cl$_2$) of the ZnTPPCl$_8$: $\lambda$=420 (Soret), 510 (weak), 550, 585 (weak) nm.

Note 4 Uv-vis spectrum (in CH$_2$Cl$_2$) of the dication [H$_4$TPPCl$_8$]$^{2+}$: $\lambda$=430 (Soret), 576, 628 nm.

Note 5 Uv-vis spectrum (in CH$_2$Cl$_2$) of the free base H$_2$TPPCl$_8$: $\lambda$=418 (Soret), 512, 588 nm. An absorption at $\lambda$=658 indicates the presence of some chlorin impurity which should be removed. An absorption at $\lambda$=550 suggests incomplete demetallation.

Note 6 The relative intensity of $\lambda$656:588 in the crude porphyrin could be as high as 1 and the complete removal of the absorption at $\lambda$=656 requires approximately 3 h. If the oxidation is not complete in 3 h, an additional 100 mg DDQ should be added.

Note 7 In general, the metal insertion is complete in 3 h. The use of an inert atmosphere during the reaction helps prevent the oxidation of Fe$^{2+}$ to Fe$^{3+}$ before insertion.

Note 8 Elution of the hemin with 5% CH$_3$OH/CH$_2$Cl$_2$ results in the partial exchange of the axial Cl ligand. Extraction with con.HCl regenerates the chloroiron-(III) species.

EXAMPLE 2

Sulfonation of H$_2$TPPCl$_8$

H$_2$TPPCl$_8$ (300 mg) is suspended in fuming sulfuric acid (14 mL) in a 25 mL 3-necked flask fitted with a reflux condenser carrying a CaSO$_4$ drying tube at the top. The suspension is heated at reflux (oil-bath temperature set at 165° C.) for 7 h when the solid dissolves to give a clear green solution. Sulfur trioxide which sublimes and deposits in the condenser has to be carefully returned to the reaction flask at regular intervals. The solution is allowed to cool overnight.

The above solution is carefully added dropwise over a period of 30 minutes to 50 mL water which is cooled in ice. The viscous solution is filtered into a 300 mL r.b. flask and treated dropwise (with stirring and cooling), with water (75 mL) followed by a suspension of NaHCO$_3$ (65 g) in water (100 mL) until it becomes slightly basic (pH 8). Towards the end, Na$_2$SO$_4$ crystallizes out, making it difficult to stir (A 1 liter flask was necessary). The solution has changed from green (usual color in acid medium) to red. Ethanol (approximately equal volume) is added to precipitate out Na$_2$SO$_4$ which is removed by filtration. Complete removal of Na$_2$SO$_4$ can not be accomplished even by chromatography (on silica gel or sephadex), dialysis and repeated recrystallizations. The compound exhibits a characteristic uv-visible spectrum of a meso tetra-substituted porphyrin (Absorption maxima in methanol: 423 nm (Soret), 521, 555, 602 and 657). Partial purification is achieved by dialysis and the sample is dissolved in minimum water (7 ml), diluted with methanol (100 ml) and crystallized by adding acetone (ca. 300 ml). A first crop yield of 212 mg is obtained and a further 105 mg are recovered from the mother liquor.

EXAMPLE 3

Synthesis of the Hemin from Sulfonated H₂TPPCl₈

A compound of the formula Ib in which:
M=Fe;
X, X°=Cl;
$X_1$=SO₃H;
$X_2$, $X_3$=H;
Y, Y°=H.

The sulfonated H₂TPPCl₈ (105 mg) is dissolved in N,N-dimethylformamide (40 mL) in a 200 mL 3-necked r.b. flask fitted with a reflux condenser. The solution is degassed by passing a slow stream of argon using a needle passed through a rubber septum and heated to reflux. At the onset of reflux, this is treated with a solution of FeCl₂.4H₂O (500 mg) in degassed N,N-dimethylformamide (10 mL). Heating is continued (with argon bubbling) and the insertion of iron is followed spectroscopically. Metallation is complete in 3 h. (UV-Vis in DMF: Soret at 424, 436 sh - double, alpha/beta at 575 and 613 sh.; UV-Vis of free base porphyrin in DMF: Soret at 425, 520, 553, 660 and 655 nm). Air is bubbled through the cooled solution overnight in order to ensure the complete oxidation of iron. Acetone (100 mL) is added dropwise with stirring and the metalloporphyrin precipitates out as a brown solid. This is recrystalized from methanol and acetone to give 120 mg.

EXAMPLE 4

Synthesis of Chloro(Meso-tetraphenyl-β-Octachloroporphinato)Iron(III) Fe(TPP.βCl₈)Cl A compound of the formula Ia in which:
M=Fe, axially ligated to Cl;
X, X°, $X_1$, $X_2$, $X_3$=H;
Y, Y°=Cl.

Step 1, Synthesis of meso-Tetraphenyl-β-octachloroporphinatonickel(II)(-NiTPP. Cl₈)

meso-Tetraphenylporphinatonickel(II) made by conventional methods, (NiTPP; 670 mg. 1 mM) is dissolved in o-dichlorobenzene (75 mL); N-chlorosuccinimide (1.6 g. 12 mM) is added and the solution heated on an oil-bath at 140° C. The reaction, monitored by uv-visible spectroscopy (NiTPP exhibits a Soret absorption at 414 nm while in the product it is shifted to 440 nm), is complete in approximately 90 min.

The solvent is removed in vacuo and the residue chromatographed on neutral alumina (Activity I, 300 g), using chloroform as the solvent. The product elutes cleanly as a reddish-yellow solution and is crystallized by concentration and addition of methanol. NiTPP.βCl₈ is collected by filtration, washed with methanol and dried.

Yield, 736 mg (78%).

Anal. Calcd for C₄₄H₂₀N₄Cl₈Ni: C, 55.81; H, 2.13; N, 5.92; Cl, 29.95.

Found: C, 55.48; H, 2.09; N, 5.76; Cl, 30.10.

¹³C NMR (75.4 MHz, CDCl₃ at 76.997) 118.995, 127.563, 129.291, 133.783, 134.399, 135.510, 140.251.

MS (m/e) Nominal mass of the most abundant peak in the isotopic cluster, 946 (M+).

UV$_{\lambda max}$(CH₂Cl₂) 440 (Soret), 554 nm.

Step 2, Demetalation of NiTPP.βCl₈

A stirred solution of NiTPP.βCl₈ (210 mg) (from Step 1, supra) in dichloromethane (70 mL) is treated with conc. sulfuric acid (50 mL) at room temperature. Within 5 min., a shiny green solid separates out from a green-brown emulsion. After a further 15 min. of stirring, the mixture is poured into ice (approx. 500 g) and more dichloromethane (total ca. 300 mL) is used to dissolve the solids. The organic layer (dichroic; yellow-green) is removed, and the aqueous layer extracted once with dichloromethane (100 mL) -trifluoroacetic acid (3 mL) and discarded. The combined organic phase is washed with water (2×250 mL), saturated aqueous sodium bicarbonate (200 mL) and dried (Na₂SO₄), meso-tetraphenyl-β-octachloroporphyrin (H₂TPP.βCl₈) is isolated by concentration and addition of methanol. Yield, 176 mg (90%).

¹³C NMR (75.4 MHz, 10% w/w CF₃CO₂H-CDCl₃, CDCl₃ at 77.141) δ, 121.922, 129.129, 129.770, 132.681, 134.236, 137.403, 141.856.

MS (m/e) Nominal mass of the most abundant peak in the isotopic cluster, 890 (M+).

UV $\lambda_{max}$(CH₂Cl₂) 452 (Soret), 552, 602, 720 nm; max (CF₃CO₂H-CH₂Cl₂) 482 (Soret), 736 nm.

Step 3, Insertion of Iron meso-Tetraphenyl-β-octachloroporphyrin (H₂TPP.βCl₈; 125 mg) from Step 2, supra is dissolved in degassed N,N-dimethylformamide (DMF, 100 mL) in a 250 mL 2-necked r.b. flask fitted with a gas inlet and a reflux condenser. The solution is heated to reflux (with N₂ bubbling) and treated with a solution of FeCl₂.4H₂O (500 mg) in degassed DMF (20 mL). The heating is continued and the insertion of iron, monitored by uv-visible spectroscopy (H₂TPP.βCl₈ exhibits a Soret absorption at 452 nm, which is shifted to 446 nm in the product), is complete in 1h. Heating is discontinued and air is bubbled through the solution overnight.

The supernatant DMF solution is decanted from the solid FeCl₃, concentrated in vacuo (ca. 60 mL) and treated with dilute HCl (1:1, 120 mL). The hemin precipitates out as a brown solid, is collected by filtration, washed thoroughly with water and dried in a vacuum dessicator.

The crude solid is dissolved in minimum CH₂Cl₂ and chromatographed on silica gel (20 g. Activity I, 230–400 mesh). Initial elution with CH₂Cl₂ removes the non-metalated starting material and the hemin is eluted with 5% CH₃OH—CH₂Cl₂. This is evaporated to dryness, and the residue is taken up in CH₂Cl₂ (100 mL) and extracted once with conc. HCl. The organic layer is washed with water (4×100 mL), dried (Na₂SO₄) and concentrated. Chloro(mesotetraphenyl-β-octachloroporphinato)iron(III) is crystallized from n-hexane and isolated (2 crops) in an overall yield of 85%.

Anal. Calcd for C₄₄H₂₀N₄Cl₉Fe: C, 53.95; H, 2.06; N, 5.72; Cl, 32.57.

Found: C, 54.36; H, 2.23; N, 5.55; Cl, 32.35.

MS (m/e Nominal mass of the most abundant peak in the isotopic clusters, 979 (M+), 944 (M+-Cl).

UV $\lambda_{max}$(CH₂Cl₂) 404/448 (Soret), 526, 564, 768 nm.

EXAMPLE 5

Synthesis of chloro[meso-tetra(2,6-dichlorophenyl)-β-octachloroporphinato]iron(III)

A compound of the formula Ia in which:
M=Fe, axially ligated to Cl;
$X^o$, X=Cl;
$X_1$, $X_2$, $X_3$=H;
Y, $Y^o$=Cl.

Chloro[meso-tetra(2,6-dichlorophenyl)porphinato]iron(III) [from Traylor et al., 1984 *J. Chem. Sci. Chem. Commun.* 279–280] (FeTPPCl$_8$Cl; 107 mg) and anhydrous ferric chloride (600 mg) are suspended in o-dichlorobenzene (15 mL) in a 50 mL 3-necked r.b. flask fitted with a gas inlet tube and a reflux condenser surmounted by a drying tube, the third neck being closed. The reaction mixture is heated on an oil-bath with stirring to 140° C. and chlorine gas is bubbled through for 5 min. The stirring is continued and the progress of the reaction is followed by uv-visible spectroscopy. [The starting material (FeTPPCl$_8$Cl) exhibits a double Soret 370/420 nm which shifts to 396/444 nm in the product (FeTPPCl$_8$βCl$_8$Cl) on completion of the reaction]. The reaction mixture is cooled and the solvent is removed in vacuo. The residue is dissolved in dichloromethane (125 mL), washed with water (2×75 mL) and chromatographed on silica gel (40 g, Activity I, 230–400 mesh). Dichloromethane is initially used to remove the β-chlorinated demetalated porphyrin and the hemin is subsequently eluted using 5% CH$_3$OH/CH$_2$Cl$_2$. The solvent is removed in vacuo, the residue redissolved in dichloromethane (200 mL) and extracted once with conc. HCl (100 mL). The organic layer is washed with water (2×100 mL) dried (Na$_2$SO$_4$) and the product crystallized from dichloromethane/n-hexane. Yield: 121 mg (88%).

Anal. Calcd for C$_{44}$H$_{12}$N$_4$Cl$_{17}$Fe: C, 42.11; H, 0.96; N, 4.46; Cl, 48.02. Found: C, 41.90; H, 1.10; N, 4.25; Cl, 48.30.

MS (m/e) Nominal mass of the most abundant peak in the isotopic clusters, 1254 (M+), 1220 (M+-Cl)

UV $\lambda_{max}$ (CH$_2$Cl$_2$) 396/444 (Soret) nm.

EXAMPLE 6

Synthesis of Chloro[meso-Tetra(Pentachlorophenyl)-β-Octachloroporphinato]Iron(III)

Fe TPPCl$_{20}$βCl$_8$.Cl

A compound of the formula Ia in which:
M=Fe, axially ligated to Cl;
X, $X^o$, $X_1$, $X_2$, $X_3$=Cl;
Y, $Y^o$=Cl.

Chloro[meso-tetra(pentachlorophenyl)porphinatoiron(III) [from Traylor et al., supra] (FeTPPCl$_{20}$.Cl; 90 mg) is dissolved in o-dichlorobenzene (15 mL) in a 50 mL 3-necked r.b. flask fitted with a gas inlet tube and a reflux condenser surmounted by a drying tube, the third neck being closed. Anhydrous ferric chloride (500 mg) is added and the solution rapidly heated to 140° C. on a preheated oil-bath. Chlorine gas is bubbled for 5 min through the stirred solution and the temperature is maintained for 1h. The strong Soret absorption of the starting material (FeTPPCl$_{20}$Cl) at 420 nm shifts to 442 nm as the chlorination goes to completion.

The solvent is removed in vacuo, and the residue is dissolved in dichloromethane (600 mL; NOTE 1) and washed with water (2×200 mL) to remove excess ferric chloride. The organic phase is dried, evaporated to dryness, and the residue is dissolved in hot chloroform (50 mL; NOTE 2) and passed through silica gel (60 g. Activity I, 230–400 mesh) placed in a fritted-glass filter funnel (150M). Washing initially with dichloromethane removes the β-chlorinated demetallated porphyrin and the hemin is subsequently eluted with 5% CH$_3$OH-CH$_2$Cl$_2$ and collected. The solvent is evaporated under reduced pressure, the residue dissolved in dichloromethane (600 mL) and extracted once with conc. HCl (200 mL). The organic phase is washed with water (3×250 mL), dried (Na$_2$SO$_4$) and the perchlorohemin (FeTPPCl$_{20}$.βCl$_8$Cl) crystallized from chloroform (NOTE 3)-n-hexane. Yield (3 crops), 77 mg (72%). MS (m/e) Nominal mass of the most abundant peak in the isotopic clusters, 1668 (M+), 1633 (M+-Cl) UV $\lambda$max (CHCl$_3$) 396/444 (Soret) nm.

NOTE 1 Due to the lower solubility of FeTPPCl$_{20}$βCl$_8$Cl (cf FeTPPCl$_8$βCl$_8$Cl) in dichloromethane, a larger volume of solvent is required to keep it in solution.

NOTE 2 The solubility of FeTPPCl$_{20}$βCl$_8$Cl in chloroform is significantly higher than in dichloromethane and is therefore a useful substitute in chromatography.

NOTE 3 Spectroscopic grade chloroform stabilized by non-polar hydrocarbon is used.

EXAMPLE 7

Synthesis of chloro[meso-tetra(4-sulfonatophenyl)-octachloroporphinato]iron(III)

A compound of the formula Ia, in which:
M=Fe, axially ligated with Cl;
X, $X^o$, $X_1$, $X_3$=H;
$X_2$=SO$_3$H;
Y, $Y^o$=Cl.

Step 1, Synthesis of meso-Tetra(4-Sulfonatophenyl)-β-octachloroporphyrin meso-Tetraphenyl-β-octachloroporphinatonickel(II) (NiTPP.Cl$_8$; 40 mg) [from Example 4] is suspended in concentrated sulfuric acid (10 mL) and immersed in an oil bath preheated to 120° C. Within 5 min. of heating, the starting material is demetalated and dissolves producing a dark green solution. Heating is continued for 5h and the solution is allowed to stir at room temperature for 12h. The reaction mixture is poured into crushed ice (50 g), neutralized (under cooling) with a saturated sodium hydroxide solution, filtered and evaporated under reduced pressure.

The residue is extracted with methanol, the methanol solution evaporated and the crude product (dissolved in minimum water) is passed over a cation exchange column (Dowex 50 WX-8, H+ form). The porphyrin fraction is collected, neutralized with sodium hydroxide, evaporated to dryness and the residue, in methanol, is further purified by chromatography on a Sephadex LH 20 column. The porphyrin is crystallized from acetone.

UV $\lambda_{max}$ (CH$_3$OH) 464 (Soret), 634, 746 nm. $\lambda_{max}$ (CH$_3$OH-NaOH) 480 (Soret), 718 nm. $\lambda_{max}$ (CH$_3$CH-H+) 486 (Soret), 722 nm.

Step 2, Insertion of Iron meso-Tetra(4-sulfonatophenyl)-β-octachloroporphyrin (30 mg) and sodium acetate (20 mg) were suspended in glacial acetic acid (40mL) and heated at 100° C. under nitrogen. A solution of $FeCl_2.4H_2O$ (70 mg) in water (1 mL) was added and the insertion of iron was followed by UV-vis spectroscopy. The reaction was complete in approximately 1h. The reaction mixture was cooled to room temperature under nitrogen and allowed to stir overnight, exposed to air.

The brown solid was filtered, washed thoroughly with acetone and dried to obtain the above-indicated product.

UV $\lambda_{max}$ (water; pH=6) 402(sh), 430 (Soret), 564, 758nm.

EXAMPLE 8

Synthesis of
Chloro[meso-tetra(2,6-dichloro-3-sulfonatophenyl)-β-octachloroporphinato]iron(III)

A compound of the formula Ia, in which:
M=Fe, axially ligated to Cl;
X, $X^o$=Cl;
$X_3$=$SO_3H$;
$X_1$, $X_2$=H;
Y, $Y^o$=Cl.

Step 1. Sulfonation

Chloro[meso-tetra(2,6-dichlorophenyl)-β-octachloroporphinato]iron(III) (30 mg) was placed in a 50 ml 3-necked r.b. flask fitted with a reflux condenser surmounted by a drying tube ($CaSO_4$) and treated with fuming sulfuric acid (10 ml). The starting material demetalated and dissolved immediately. The resulting green solution was heated at 165° C. on an oil-bath for 7h. Condensation of sulfur trioxide inside the condenser was minimized by adjusting the cooling water as required. The reaction mixture was allowed to stir at room temperature overnight and poured carefully into ice (200 g).

The aqueous solution [UV: 468(Soret), 602, 640, 702 nm.], was neutralized with a saturated solution of NaOH, ethanol (200 ml) added and cooled. The sodium sulfate crystallized was filtered, the filtrate concentrated (10 ml), diluted with ethanol and filtered again. The filtrate was evaporated to dryness, dissolved in minimum water and passed through Dowex 50 W-X8 ion-exchange resin ($H^+$ form). The eluate was neutralized with dilute sodium hydroxide, evaporated to dryness, redissolved in methanol and the product crystallized from acetone. Yield, 36 mg (2 crops). UV $\lambda_{max}$ (DMF) 474(Soret), 584(sh) 626, 680 nm.

Step 2. Insertion of Iron

The porphyrin prepared as described above (15 mg) was dissolved in N,N-dimethylformamide (10 ml) in a 50 ml 3-necked r.b. flask and degassed by passing a stream of nitrogen for 1h. The solution was heated to reflux and treated with 1 ml of a stock solution of $FeCl_2.4H_2O$ (220 mg) in N,N-dimethylformamide (DMF, 5 ml). An immediate color change from green to yellow-brown was observed. Refluxing was continued for 15 min. and a UV spectrum [$\lambda_{max}$ in DMF: 452(Soret), 582, 630] indicated that the metalation was complete. The reaction mixture was allowed to cool and stir at room temperature overnight (exposed to air). Acetone (50 ml) was added, the product collected by filtration and crystallized from methanol-acetone.

UV: $\lambda_{max}$ ($CH_3OH$) 448 (Soret), 572, 660 nm.

EXAMPLE 8

The product was further purified by ion-exchange chromatography (aqueous solution; Dowex 50W-X8 $H^+$ form) followed by crystallization from acetone.

UV $\lambda_{max}$ (water; pH=6) 422 (Soret) nm. $\lambda_{max}$ (water; pH=9) 402(sh), 426 (Soret), 604, 656(sh), 740nm.

EXAMPLE 9

Catalyzing the oxidation of lignin model compounds with $FeTPPCl_8S$.

Three lignin model compounds, 1,4-dimethoxybenzene, a β-O-4 model (arylglycerol β-aryl ether substructure of lignin) and a β-1 model (aryl glycerol-β-aryl substructure of lignin [see Kersten et al. 1985 *J. Biol. Chem.* 260:2609–2612; Tien et al. 1983 *Science* 221:661–663; and Kirk et al. 1986 *Biochem, J.* 236:279–287] are reacted with an iron (III) (tetraphenyloctachloro)sulfonatoporphyrin ($FeTPPCl_8S$). A final concentration of 50 μM $FeTPPCl_8S$ is reacted with 5 mM final concentration of the oxidant t-butyl peroxide. The results indicate that Fe $TPPCl_8S$ mimics the enzyme ligninase.

Using 1,4-dimethoxybenzene as a substrate, the $FeTPPCl_8S$ produced spectral changes, but unlike ligninase does not form the benzaquinone product.

The β-O-4 model with $FeTPPCl_8S$ yields the same products as with ligninase, and, in addition demethoxylates to a greater extent than ligninase. Products that are produced include veratrylaldehyde and, and in addition, a trace of veratric acid which has not been observed with the ligninases, hence further indicating the greater oxidative potential of the porphyrins compared to the ligninases.

The β-1 model with $FeTPPCl_8S$ yields methanol as well as other products as with ligninase, including veratrylaldehyde and trace amounts of veratric acid.

EXAMPLE 10

Treatment of lignin with the porphyrins of Examples 7 and 8.

250 μg of the Kraft softwood lignin Indulin AT (Westvaco Corporation, Charleston Heights, S.C.) is dissolved in 2 ml DMF. Peracetic acid is used as the oxidant at a final concentration of 1.84 μM. In separate experiments the porphyrins of Examples 7 and 8, above, are used at a final concentration of 500 μM. The reaction mixture is stirred at room temperature for 24 hours and the resulting products are analyzed by gel permeation chromatography using a TSK 4000 column with 1:1 Chloroform:Dioxane (Phenomenex, Rancho Palos Verdes, Calif.). Absorbance is monitored at 280 nanometers, and in each case a distinct shift of the peaked area to the right indicating a degradation of the lignin was observed.

EXAMPLE 11

Treatment of veratryl alcohol with porphyrin manganese octachlorotetrasulfonatoporphyrin Veratryl alcohol, a lignin-related compound, at a 1 mM final concentration is reacted with 1 μM manganese octachlorotetrasulfonato porphyrin ($MnTPPCl_8S$) in water at room temperature. Various oxidants are present, including hydrogen peroxide, sodium hypochlorite, t-butylperoxide, cumylhydroperoxide, potassium iodate, and iodosyl benzene, as shown in Table 1, below. The concentration of oxidants ranges from 50–100 mM and pH is from 1–10. The product is veratrylaldehyde. Its yield is dependent upon the oxidant and the pH.

TABLE I

MnTPPCl$_8$S* Reaction with Veratryl Alcohol**

| Oxidant | Concentration of Oxidant | pH | Production of Veratrylaldehyde | Time (Minutes) |
|---|---|---|---|---|
| NaOCl | 0.067 mM | 7 | .0072 | 10 |
| tBuOOH | 0.1 mM | — | .00104 | 64 |
| phenyl t-butyl hydroperoxide | 0.1 mM | — | .0013 | 90 |
| H$_2$O$_2$ | 0.1 mM | pH = 2 | .0013 | 183 |
| H$_2$O$_2$ | 0.1 mM | Neutral | .00054 | 63 |
| H$_2$O$_2$ | 0.1 mM | pH = 10 | .0076 | 9 |
| C$_6$H$_5$IO | 0.05 mM | — | .022 | 10 |
| C$_6$F$_5$IO | 0.064 mM | — | .019 | 11 |

*Concentration of MnTPPCl$_8$S = 1 μM
**Concentration of veratrylalcohol = 1 mM

EXAMPLE 12

Treatment of veratryl alcohol with iron octachlorotetraphenylosulfonatoporphyrin The same general procedure as set forth in Example 11 is followed, except the catalyst is iron octachlorotetraphenylosulfonatoporphyrin. Results are given in Table 2, below.

| Oxidant | Concentration of Oxidant | pH | Production of Veratrylaldehyde mM | Time (Minutes) | Yield of veratrylaldehyde versus oxidant (molar basis) |
|---|---|---|---|---|---|
| NaOCl | 0.067 mM | — | .0000022 | 3 | 19% |
| tBuOOH | 0.01 mM | — | .0424 | 15.5 | 50% |
| Cumyl-hydroperoxide | 0.1 mM | — | .0428 | 7 | 49% |
| KIO$_4$ | 0.1 mM | pH = 2 | .0085 | 864 | 68% |
| Meta-chloroperbenzoic acid | 0.1 mM | — | .0047 | 16 | 10% |
| H$_2$O$_2$ | 0.1 mM | pH = 1.5 | .019 | 5.5 | 20% |
| H$_2$O$_2$ | 0.1 mM | Neutral | .018 | 9 | 12% |
| H$_2$O$_2$ | 0.1 mM | pH = 10 | .0046 | 5.5 | 5% |
| C$_2$H$_5$IO | 0.05 mM | — | .0087 | 7 | 30% |
| C$_6$F$_5$IO | 0.064 mM | — | .017 | 28 | 28% |

— pH not adjusted
*Concentration of FeTPPCl$_8$S = 1 μM
**Concentration of veratrylalcohol = 1 mM

EXAMPLE 13

Catalytic Efficiency of β-Chlorinated-Meso-Tetraphenylhemins

The catalytic activities of the hemins FeTPPCl$_8$.βCl$_8$.Cl and FeTPPCl$_{20}$.βCl$_8$Cl are examined in hydroxylation reactions (cyclohexane as substrate) and epoxidation reactions (cyclohexene as substrate) as described below:

Iodosopentafluorobenzene (2.0 mg, $6.4 \times 10^{-2}$ mol.dm$^{-3}$) is mixed with the substrate (1.0 mol.dm$^{-3}$) in dichloromethane in a culture tube with a silicon rubber septum. The catalyst, in dichloromethane $(1.0 - \times 10^{-4}$ mol.dm$^{-3})$ is introduced and the reaction mixture is mixed constantly until either the solid disappears or the catalyst is destroyed. The yields of the products are determined by GLC (Carbowax 20M and SE 30), and the results are compared with those of octachlorohemin (FeTPPCl$_8$.Cl) and are summarized below in Table 5.

TABLE 5

| Substrate | Product | % Yields Based on Oxidant | | |
|---|---|---|---|---|
| | | FeTPPCl$_8$Cl | FeTPPCl$_8$βCl$_8$Cl | FeTPPCl$_{20}$βCl$_8$Cl |
| Cyclohexane | Cyclohexanol | 23.6 | 42.1 | 57.1 |
| Cyclohexene | Cyclohexene oxide | 57.9 | 58.7 | 62.2 |
| | Cyclohex-2-ene-1-ol | 5.0 | 4.1 | 5.0 |
| | Cyclohex-2-ene-1-one | 6.2 | 5.9 | 7.6 |

EXAMPLE 14

Preparation of chloro[meso-tetra-(4-carboxyphenyl)-β-octachloroporphinata]iron(III) - compound of the formula I in which Y and Y$^o$ are chloro, X, X$^o$, X$_1$ and X$_3$ are H, X$_2$ is carboxy and M is Fe(Cl).

A compound such as that above named is preferably prepared sequently by 1) reacting p-carboxybenzaldehyde methyl ester with pyrrole in a conventional manner to obtain the free base porphyrin; 2) inserting Ni to form the Ni-bearing porphyrin (M=Ni) in a conventional manner; 3) chlorinating with chlorosuccinimide the Ni-bearing porphyrin in a manner described herein to form the carboxy-substituted phenyl-β-octachlorinated porphyrin containing the Ni; 4) removing the Ni in a manner described herein to form the corresponding free base porphyrin; 5) removing the methyl ester in a conventional manner to form the free acid; and 6) inserting Fe using FeCl$_2$ in a manner indicated herein for the analogous compound. Following this procedure, the above-named porphyrin was prepared and ascertained to catalytically effective.

The above-named porphyrin may also be prepared starting with the free base meso-4-carboxyphenylporphyrin, a known compound, methyl-esterifying the carboxy groups and then proceeding as indicated in Steps 2 through 7, above.

EXAMPLE 15

Treatment of Pulp

Northern softwood kraft pulp (consistency 2.5%) in the amount of 2g. was incubated in separate experiments with 2.5% (w/v) sodium hydroxide in the presence of 10 mM of t-butyl peroxide in the absence of a porphyrin as control or in the presence of 10 mM of the porphyrin of Example 7.

The above experiments were repeated using 50 mM of sodium citrate instead of sodium hydroxide.

The two sets of above experiments were repeated upon using 0.5% (w/v) sodium perclilorate in place of the t-butyl peroxide, except that the perchlorate/citrate combinations were omitted.

All of the above sets of experiments were then repeated using the porphyrin of Example 8 instead of that of Example 7.

In each set of experiments the Kappa number of the control and prophyrin treated pulp samples was measured and compared after all treated pulps were extracted with alkali in a conventional manner. A generally greater reduction in Kappa number was observed with the porphyrin containing experiments with a greater being indicated with the use of the sodium perchlorate.

EXAMPLE 16

Treatment of Pulp with the Porphyrins:

A: meso-Tetra(2,6-dichloro-3-sulfonatophenyl)-β-octachloroporphinatoiron(III), and B: meso-Tetra(4-sulfonatophenyl)-β-octachloroporphinatoiron(III):

A series of samples (2 g.) of Northern softwood kraft were each washed with 500 ml deionized water, filtered, and then placed in 80 ml Na-citrate buffer (50 mM, pH 5) at 60° C. Tert-butyl hydroperoxide was added to 0.5% (w/v) followed by the addition of the porphyrin. The samples were stirred in an oven at 60° C. for 18 hours at which time they were washed with approximately 1.5 liters of buffer, added to 80 ml of 2.5% (w/v) sodium hydroxide (60° C.) and stirred in an oven at 60° C. for an additional 90 minutes. The samples were then washed with 2.5 liters of deionized water. Kappa measurements were made on all samples to determine the decrease in lignin content, and the results reported below.

| Porphyrin | t-Butyl Hydroperoxide | Kappa |
| --- | --- | --- |
| none | none | 17.9 |
| none | 0.5% (w/v) | 17.6 |
| A: 0.45 mg | 0.5% | 10.4 |
| A: 0.90 mg | 0.5% | 9.5 |
| B: 0.45 mg | 0.5% | 16.4 |
| B: 0.90 mg | 0.5% | 14.7 |

What is claimed is:

1. The method of modifying or degrading lignin in wood or pulp comprising treating the wood with a lignin modifying or degrading effective amount of a compound of the formula:

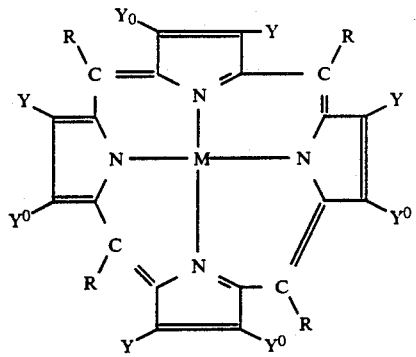

wherein M is a transition metal capable of sustaining oxidation, said M being optionally axially ligated to a ligand, each Y and $Y^o$ is independently H, fluoro or chloro, each R ring is

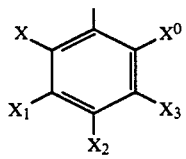

X and $X^o$ are independently H or a non-water solubilizing electronegative group, and $X_1$, $X_2$ and $X_3$ are independently H or an electronegative group, subject to the provisos that:

1) when none of $X_1$, $X_2$ and $X_3$ is in a water solubilizing group, then at least one of Y and $Y^o$ on each porphyrin ring is other than H,
2) when Y and $Y^o$ are both H, at least one but not more than two of $X_1$, $X_2$ and $X_3$ is a water solubilizing group and at least two of X, $X^o$, $X_1$, $X_2$ and $X_3$ is a non-water solubilizing electronegative group, or the water soluble salts thereof in which said water solubilizing groups are in corresponding water soluble salt form, and
3) no more than two of $X_1$, $X_2$ and $X_3$ is a water solubliizing group, or a compound of the formula I in which the water solubilizing groups are in water soluble salt form.

2. The method of claim 1 in which the wood is in the form of wood chips.

3. The method of claim 1 in which the wood is thermal mechanical pulp.

4. The method of claim 2 in which kraft pulp is bleached.

5. A method according to claim 1 wherein
X and $X^o$ are independently H, fluoro, chloro, bromo or $NO_2$, and
$X_1$, $X_2$ and $X_3$ are independently H, fluoro, chloro, bromo, $SO_3H$, COOH or $NO_2$, subject to the provisos that
1) when none of $X_1$, $X_2$ and $X_3$ is $SO_3H$ or COOH, then at least one Y and $Y^o$ on each porphyrin ring is other than H,
2) when Y and $Y^o$ are both H, at least one but not more than two of $X_1$, $X_2$ and $X_3$ is $SO_3H$ or COOH, and at least two of X and $X^o$ and the $X_1$, $X_2$ and $X_3$ which are not $SO_3$ or COOH are independently fluoro, chloro, bromo, or $NO_2$ and 3) no more than two of $X_1$, $X_2$ and $X_3$ are $SO_3H$ or COOH, or a compound of formula I in which $SO_3H$ and COOH groups are in water soluble salt form.

6. A method according to claim 5 wherein each Y and $Y^o$ independently H, fluoro or chloro, and at least one Y and $Y^o$ on each porphyrin ring is fluoro or chloro.

7. A method according to claim 1 wherein
M is Fe;
X, $X^o$, $X_1$, $X_2$ and $X_3$ are H; and
Y and $Y^o$ are Cl.

8. A method according to claim 1 wherein
M is Fe;
$X^o$ and X are Cl;
$X_1$, $X_2$ and $X_3$ are H; and
Y and $Y^o$ are Cl.

9. A method according to claim 1 wherein
M is Fe; and
X, $X^o$, $X_1$, $X_2$, $X_3$, Y and $Y^o$ are Cl.

10. A method according to claim 1 wherein
M is Fe;
X, $X^o$, $X_1$ and $X_3$ are H;
$X_2$ is $SO_3H$; and
X and $Y^o$ are Cl.

11. A method according to claim 1 wherein
M is Fe;
X and $X^o$ are Cl;
$X_1$ and $X_2$ are H;
$X_3$ is $SO_3H$; and
Y and $Y^o$ are Cl.

12. In the method of hydroxylating an alkane or cycloalkane by oxidation in the presence of a catalytic effective amount of a porphyrin, the improvement comprising employing therein as the porphyrin a compound of the formula:

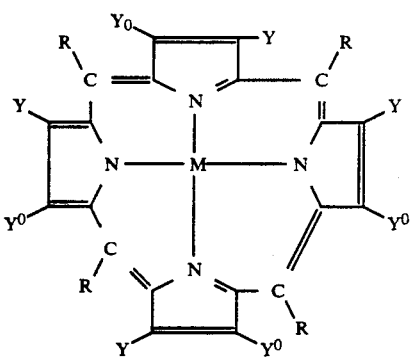

wherein M is a transition metal capable of sustaining oxidation, said M being optionally axially ligated to a ligand, each Y and $Y^o$ is independently H, fluoro or chloro, each R ring is

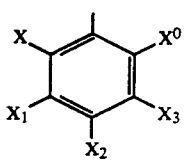

X and $X^o$ are independently H or a non-water solubilizing electronegative group, and $X_1$, $X_2$ and $X_3$ are independently H or an electronegative group, subject to the provisos that:

1) when none of $X_1$, $X_2$ and $X_3$ is in a water solubilizing group, then at least one of Y and $Y^o$ on each porphyrin ring is other than H,
2) when Y and $Y^o$ are both H, at least one but not more than two of $X_1$, $X_2$ and $X_3$ is a water solubilizing group and at least two of X, $X^o$, $X_1$, $X_2$ and $X_3$ is a non-water solubilizing electronegative group, or the water soluble salts thereof in which said water solubilizing groups are in corresponding water soluble salt form, and
3) no more than two of $X_1$, $X_2$ and $X_3$ is a water solubilizing group, or a compound of the formula I in which any water solubilizing groups is in water soluble salt form.

13. The method of claim 12 in which the hydroxylation is carried out in an inert organic solvent in which the porphyrin is dissolved.

14. A method according to claim 12 wherein
M is Fe;
X, $X^o$, $X_1$, $X_2$ and $X_3$ are H; and
Y and $Y^o$ are Cl.

15. A method according to claim 12 wherein
M is Fe;
X and $X^o$ are Cl;
$X_1$, $X_2$ and $X_3$ are H; and
Y and $Y^o$ are Cl.

16. A method according to claim 12 wherein
M is Fe; and
X, $X^o$, $X_1$, $X_2$, $X_3$, Y and $Y^o$ are Cl.

17. A method according to claim 12 wherein
M is Fe;
X, $X^o$, $X_1$ and $X_3$ are H;
$X_2$ is $SO_3H$; and
Y and $Y^o$ are Cl.

18. A method according to claim 12 wherein
M is Fe;
X and $X^o$ are Cl;
$X_1$ and $X_2$ are H;
$X_3$ is $SO_3H$; and
Y and $Y^o$ are Cl.

19. In the method of epoxidizing an alkene or cycloalkene by oxidation in the presence of a porphyrin, the improvement comprising employing therein as the porphyrin a compound of the formula:

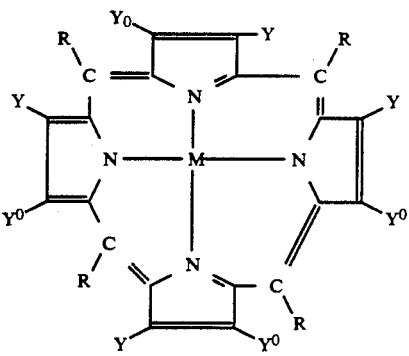

wherein M is a transition metal capable of sustaining oxidation, said M being optionally axially ligated to a ligand, each Y and $Y^o$ is independently H, fluoro or chloro, each R ring is

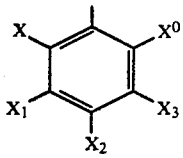

X and $X^o$ are independently H or a non-water solubilizing electronegative group, and $X_1$, $X_2$ and $X_3$ are independently H or an electronegative group, subject to the provisos that:

1) when none of $X_1$, $X_2$ and $X_3$ is in a water solubilizing group, then at least one of Y and $Y^o$ on each porphyrin ring is other than H,
2) when Y and $Y^o$ are both H, at least one but not more than two of $X_1$, $X_2$ and $X_3$ is a water solubilizing group and at least two of X, $X^o$, $X_1$, $X_2$ and $X_3$ is a non-water solubilizing electronegative group, or the water soluble salts thereof in which said water solubilizing groups are in corresponding water soluble salt form, or a compound of the formula I in which the water solubilizing groups are in water soluble salt form,
3) no more than two of $X_1$, $X_2$ and $X_3$ is a water solubilizing group, or a compound of the formula I in which any water solubilizing groups is in water soluble salt form.

20. The method of claim 19 in which the epoxidation is carried out in an inert organic solvent in which the porphyrin is dissolved.

21. A method according to claim 19 wherein
M is Fe;
X, $X^o$, $X_1$, $X_2$ and $X_3$ are H; and
Y and $Y^o$ are Cl.

22. A method according to claim 19 wherein
M is Fe;
X and $X^o$ are Cl;
$X_1$, $X_2$ and $X_3$ are H; and
Y and $Y^o$ are Cl.

23. A method according to claim 19 wherein
M is Fe; and
X, $X^o$, $X_1$, $X_2$, $X_3$, Y and $Y^o$ are Cl.

24. A method according to claim 19 wherein
M is Fe;
X, $X^o$, $X_1$ and $X_3$ are H;
$X_2$ is $SO_3H$; and
Y and $Y^o$ are Cl.

25. A method according to claim 19 wherein
M is Fe;
X and $X^o$ are Cl;
$X_1$ and $X_2$ are H;
$X_3$ is $SO_3H$; and
Y and $Y^o$ are Cl.

* * * * *